(12) United States Patent
Barth

(10) Patent No.: US 8,597,437 B2
(45) Date of Patent: Dec. 3, 2013

(54) BIOCOMPATIBLE MATERIAL MADE OF STAINLESS STEEL HAVING A MARTENSITIC SURFACE LAYER

(76) Inventor: Peter Barth, Schelklingen (DE)

( * ) Notice: Subject to any disclaimer, the term of this patent is extended or adjusted under 35 U.S.C. 154(b) by 277 days.

(21) Appl. No.: 13/122,895

(22) PCT Filed: Sep. 19, 2009

(86) PCT No.: PCT/DE2009/001292
§ 371 (c)(1),
(2), (4) Date: Jun. 2, 2011

(87) PCT Pub. No.: WO2010/040333
PCT Pub. Date: Apr. 15, 2010

(65) Prior Publication Data
US 2012/0101531 A1 Apr. 26, 2012

(30) Foreign Application Priority Data

Oct. 8, 2008 (DE) .......................... 10 2008 050 458
Oct. 8, 2008 (DE) .......................... 20 2008 015 481
Dec. 8, 2008 (DE) .......................... 10 2008 060 681

(51) Int. Cl.
*C23C 8/26* (2006.01)
*C22C 38/18* (2006.01)

(52) U.S. Cl.
USPC .......................................... 148/318; 148/230

(58) Field of Classification Search
USPC .......................................... 148/317, 206–239
See application file for complete search history.

(56) References Cited

U.S. PATENT DOCUMENTS

| 8,349,094 B2* | 1/2013 | Boerner et al. ............... 148/318 |
| 2006/0130934 A1* | 6/2006 | Kuroda et al. ................ 148/221 |
| 2007/0217293 A1* | 9/2007 | Takasawa ..................... 368/280 |

FOREIGN PATENT DOCUMENTS

| DE | 40 33 706 | 2/1990 |
| DE | 10 2004 039926 | 2/2006 |
| EP | 0 652 300 | 5/1995 |
| EP | 1 579 886 | 9/2005 |
| EP | 1 837 414 | 9/2007 |
| EP | 1 956 099 | 8/2008 |
| JP | 58084968 A * | 11/1981 |

* cited by examiner

Primary Examiner — Deborah Yee
(74) Attorney, Agent, or Firm — Fay Kaplun & Marcin, LLP

(57) ABSTRACT

A biocompatible material is made of a rust-resistant, alloyed stainless steel which is configured with at least one martensitic surface layer which is formed by a heat treatment with nitrogen case hardening and subsequent cooling. The surface layer, orthogonally to the surface into the sample interior, displaying a virtually linear course of the accompanying hardening and being achieved by a complete phase change (so-called austenitising) in the structural state from ferrite via austenite to martensite. In addition, the biocompatible material is in contact preferably indirectly or directly with the human body, no reactions and/or sensitivity problems being able to occur even in permanent use as a result of its absolute freedom from nickel.

14 Claims, 3 Drawing Sheets

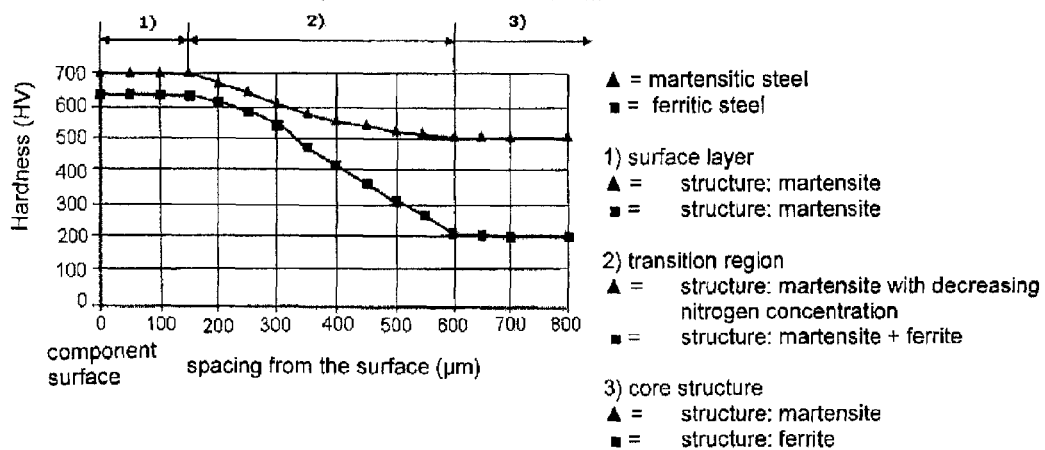

Figure 1a: shows the hardness course with a component thickness of 5.00 mm

▲ = martensitic steel
■ = ferritic steel 1) surface layer
▲ = structure: martensite
■ = structure: martensite 2) transition region
▲ = structure: martensite with decreasing nitrogen concentration
■ = structure: martensite + ferrite 3) core structure
▲ = structure: martensite
■ = structure: ferrite

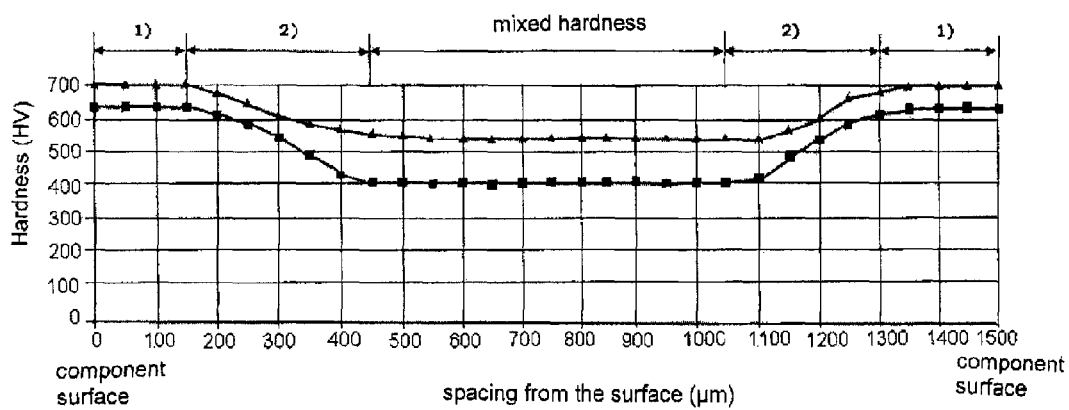

Figure 1b: shows the hardness course with a complnent thickness of 1.5 mm

Figure 1c: shows the penetrable hardness course with a component thickness of 0.5mm
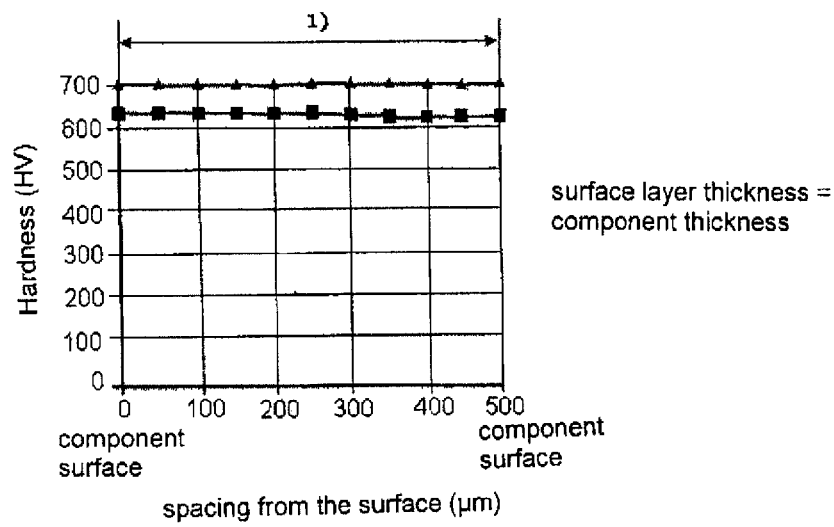
surface layer thickness = component thickness
Figure 1d: transverse section through heat-treated ferrite steel
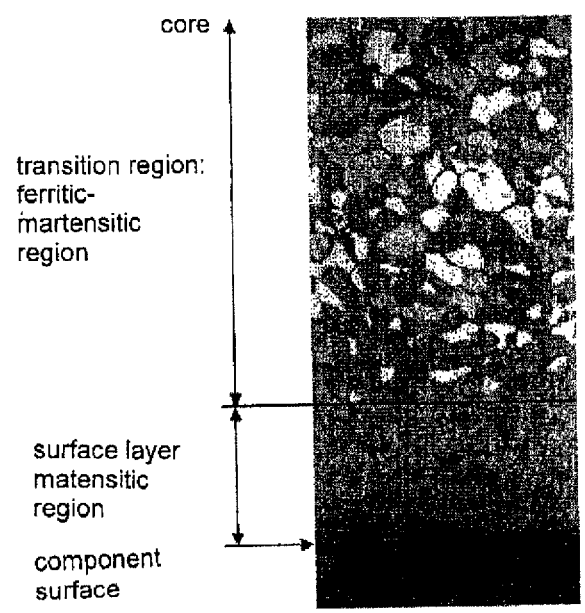

BIOCOMPATIBLE MATERIAL MADE OF STAINLESS STEEL HAVING A MARTENSITIC SURFACE LAYER

FIELD OF INVENTION

The invention relates to a biocompatible material made of stainless steel which is formed from a rust-resistant, alloyed stainless steel and has at least one martensitic surface layer.

BACKGROUND INFORMATION

In recent years, stainless steel jewellery has become more and more important and is sold on an ever increasing scale. Watches made of stainless steel, in contrast, have been known already for a fairly long time and appear correspondingly widely on the market. However, the austenitic steel used at present, both in the sphere of watches and jewellery, has the extremely negative property that this stainless steel, in contrast to silver, gold or titanium jewellery, has a high alloy component of nickel which gives this material very negative aspects with respect to the production of e.g. watches and/or jewellery and/or implants. The greatest disadvantage hereby is the fact that most people react to nickel with allergic reactions and/or sensitivity problems and they must consequently avoid nickel-containing materials of any type on or in the body in order to be able to prevent allergies.

A further disadvantage of the austenitic stainless steels used to date for stainless jewellery and/or watches and/or implants, in addition to the high and very negative nickel content, is that the scratch-resistance thereof, in particular the surface hardness thereof (with approx. 200 HV), can in fact be increased by means of hardening methods which are known in general and described subsequently in order to reduce scratching of the manufactured products, e.g. during use or when worn, but has, at the same time, the extreme By means of known processes, such as e.g. TiC, TiN, PVD, DLC . . . , a hard material layer which is in fact very hard but only very thin (a few μm) can in fact be applied on the surface of the austenitic steel. However, these thin layers have the disadvantage that, during mechanical loading, above all during mechanical point loading, they break down or flake off. The reason for this resides in the fact that the hardness decreases abruptly under the hardened layer to the initial hardness (approx. 200 HV) of the steel used. This effect is generally known in the literature as "the eggshell" effect.

Furthermore, these austenitic steels can in fact be hardened permanently with a hard and better impact-resistant surface (up to approx. 1800 HV) by the generally known low-temperature process "Kolsterising". Carbon at below 300° C. is hereby diffused in during a process duration of 5 to 6 days. The disadvantage of this method is however the extremely long process duration and the very high production costs associated therewith. In addition, the relatively small layer thickness at up to at most 33 μm is also extremely negative here since the hardness inside this gradient-associated layer decreases relatively rapidly to the initial hardness of the austenitic steel (approx. 200 HV). A further great disadvantage of these hardened or unhardened austenitic steels is their very high nickel content.

One hardening process for a martensitic steel (AISI 410) is known from Corrosion Science 48 (2006) 2036-2049 by C. X. Li et al. relating to a plasma-nitriding process in the low-temperature range between 420-500° C. It is disadvantageous here again that the applied hardness at above 1000 HV decreases almost abruptly, i.e. with a virtually abrupt drop and clearly detectable phase boundary, to the initial hardness (eggshell effect), which has the result that collision or impact energy, e.g. in the form of point loading, can only be partially absorbed, i.e. with poor impact-strength resistance and hence breaking down of the hard layer is very probable. Furthermore, it is known from Davis et al., ASM Handbook, Volume 4, Heating Treating 1991, AMS International US, to nitride also steels of the type AISI 430 and 460 in the low-temperature range up to at most 595° C.

In the case of these cited low-temperature processes (nitriding and plasma-nitriding) for the indicated steels in the temperature range up to at most 595° C., in fact nitrogen diffuses into the steel surface but no phase conversion/austenitising takes place. A further great disadvantage of these steels after treatment thereof is that they are not corrosion-resistant. In addition, the very high process times between 20 and 48 hours and the significantly higher production costs, associated therewith, are disadvantageous.

To date, ferritic chromium steels have been seen as non-hardenable by means of a heat treatment on the basis of the too low carbon content according to the general state of the art, and above all—in comparison with austenitic steels—also as non-corrosion-resistant steels.

Martensitic chromium steels could in fact be hardened previously by specific hardening processes, such as e.g. case hardening with carbon, but the free chromium component and hence the corrosion-resistance thereof is significantly reduced.

For this reason, there is still a great need to improve a biocompatible material made of stainless steel for all products which can be worn on or borne inside the body such that the chromium steel used is distinguished by approximately the same production costs in addition to the required important freedom from nickel and simultaneous excellent scratch-resistance/hardness and corrosion-resistance.

Since with all types of jewellery, watches and implants or all products which are worn on or borne partially inside or completely inside the body, direct and partially also permanent body contact with the material used exists, the requirement to use exclusively a nickel-free material in order to avoid allergic reactions or sensitivity problems is particularly high. In order in addition to prevent or to reduce scratching and rusting due to wear and use, the requirement exists in addition to use a highly scratch-resistant and corrosion-resistant material for all types of jewellery, watches and implants. In order to ensure the profitability of the objects according to the invention, such as jewellery, watches and implants, the production costs should not be increased but advantageously remain approximately the same.

In the prior art described above, hard material layers can in fact be applied on the presently used austenitic steels via TiC, TiN, PVD, DLC . . . , or by Kolsterising, for biocompatible materials (such as e.g. watches/parts for watches, all types of jewellery and implants), however the layer thicknesses produced therewith are very thin and break down very rapidly or flake off upon mechanical point loading because of the abrupt decrease in hardness to the initial hardness of approx. 200 HV. In this case, not only are the applied layers very thin and, without a supporting transition layer, disadvantageous, but also the required additional extremely long process times and the significant increase in production costs associated therewith. For biocompatible materials which are worn on or borne partially inside or completely inside the body, such as e.g. all types of jewellery, watches/parts for watches and implants, economical production with these methods is virtually precluded.

In the case of the described hardening processes (nitriding and plasma-nitriding) for martensitic steels, the loss of corrosion-resistance is in addition very disadvantageous and hence precludes application entirely for the products according to the invention.

SUMMARY OF INVENTION

The present invention relates to biocompatible material made of stainless steel which is superior to the prior art and which has, at the same time, in addition to approximately the same production costs and additional absolute freedom from nickel, such high scratch-resistance that scratching is extensively avoided and corrosion-resistance also during long term use in the body and/or partially inside the body and/or completely inside the body is achieved and allergic reactions and/or sensitivity problems should be precluded entirely because of the freedom from nickel.

According to the invention, it is hence proposed that a rust-resistant, alloyed stainless steel is used for the biocompatible material of the invention, the production costs remaining virtually the same and the material being located predominantly on and/or partially inside the body and/or completely inside the body and being present with at least one martensitic surface layer produced by a heat treatment and the material being completely nickel-free.

According to the invention, there is understood by biocompatible material made of stainless steel that it hereby involves rust-resistant, alloyed chromium steels, more precisely ferritic and/or martensitic and/or ferritic/martensitic chromium steels which are nickel-free, and consequently all those sorts of allergy problems which can be attributed to nickel can be completely precluded even during long-lasting or permanent body contact outside and inside the body.

There is hereby understood by freedom from nickel or nickel-free that the chromium steel which is used comprises no nickel as alloy component.

With the invention, a significantly higher resistance relative to mechanical point loading, in total more economical production costs, very good corrosion-resistance and furthermore the extremely important freedom from nickel of the material used for the products according to the invention is made possible at the same time because of the surface layer.

Because of the lack of the nickel component and the accompanying significantly cheaper supply price of the chromium steel according to the invention and the additionally improved machinability, the production costs, despite heat treatment, are approximately the same as those for the untreated austenitic steels which are used at present for the objects, such as watches, jewellery and implants.

As a result of the heat treatment, the use of chromium steels according to the invention becomes possible for the first time, which, because of the martensitic surface layer in combination at the same time with freedom from nickel, prove to have corrosion-resistance, high scratch-resistance with almost the same production costs. When using the chromium steels according to the invention for objects such as watches and jewellery, the freedom from nickel is at least just as important as high scratch-resistance with simultaneous corrosion-resistance in order to be able to preclude completely allergic reactions which can be attributed to nickel by use and/or by wearing on the body or partially inside the body. The scratch-resistance is not so elementary with implants but the freedom from nickel, in addition to simultaneous corrosion-resistance, is exceptionally important here also.

There is intended by the surface layer according to the invention, that layer which, orthogonally to the surface into the sample interior, displays a martensitic configuration of the structure and a virtually linear course of the accompanying hardening after the heat treatment. This martensitic surface layer is achieved by a complete phase conversion (so-called austenitising) of the structural state of ferrite via austenite to martensite by means of the heat treatment, the thickness of the surface layer produced being dependent upon the duration of the heat treatment and the process parameters thereof and upon the sample thickness. This means that this martensitic surface layer can also be completely penetrable in the case of sufficiently thin samples and hence the complete structure of the sample changes from ferrite via austenite to martensite over the complete sample cross-section. The term surface layer in the sense of the invention hence also comprises embodiments in which the material is formed completely from the surface layer.

In the case of sufficiently thick samples, the layer thickness of the surface region can be adjusted and adapted correspondingly to the requirements of the components. Typical surface layer thicknesses are between 80 to 300 μm.

Of course, thinner surface layers can also be produced for a biocompatible material (e.g. watch base, necklace, earring, etc.) which experiences no mechanical point loadings, as experience shows. However, it is essential to the invention that the surface layer has a thickness of at least 20 μm in order to be able adequately to withstand sufficient protection or, without damaging the surface layer after the heat treatment, any polishing or matting which is undertaken.

The so-called austenitising takes place, in the case of martensitic chromium steels, analogously to ferritic chromium steels, from ferrite via austenite to martensite since the initial structure, i.e. the untreated martensitic chromium steel, likewise has a purely ferritic structure.

There is hereby intended by a virtually linear course of the accompanying hardening inside the martensitic surface layer that, inside this surface layer, there can be a maximum difference in hardness values of 20%, measured according to Vickers hardness test HV1.

The surface layer can thereby be configured to be single-sided or multiple-sided or preferably encasing the core since the heat treatment is effected preferably completely on all sides of the sample.

If the material has a surface layer of a defined thickness, a transition region can abut thereon.

The transition region differs, in the structure configuration, compared with the surface region between ferritic and martensitic chromium steels.

In the case of the transition region of a ferritic chromium steel, that region is intended which abuts directly on the surface layer likewise orthogonally to the surface into the sample interior. In the case of this transition region, no complete phase conversion on the basis of the heat treatment is achieved, instead it consists of a mixed structure of the initial ferrite and the formed martensite. This means that, in this transition region, no complete phase conversion by the heat treatment is achieved because of the deeper position. The thickness of this transition region is, analogously to the surface region, dependent upon the sample thickness and shows a virtually linear decrease in accompanying hardness inside this region and can be adjusted via the duration of the heat treatment and the process parameters thereof and correspondingly adapted to the requirements of the components.

In the case of the transition region of a martensitic chromium steel, that region is intended which abuts analogously directly on the surface layer likewise orthogonally to the surface into the sample interior. In the case of this chromium steel, the transition region consists of a martensitic structure with decreasing nitrogen concentration in the direction of the sample interior. The thickness of this transition region is, analogously to the surface region of the ferritic chromium steel, dependent upon the sample thickness and shows a virtually linear decrease in accompanying hardness inside this region and can also be adjusted via the duration of the heat treatment and the process parameters thereof and adapted correspondingly to the requirements of the components. Typical transition regions are between 100 to 600 μm.

The surface layer and transition zone of the biocompatible material, formed by the heat treatment, and of the, associated therewith, non-abrupt but virtually linear hardness in the surface layer and continuously decreasing hardness in the transition zone, the chromium steel according to the invention shows a significantly higher impact-strength than the previously known and described hardening processes.

The invention thereby also jointly includes embodiments in which the surface layer has another small component, as a function of embedded C and N content of the steel material, of residual austenite.

There is understood by the term "biocompatible material", a material which is applied on the body or at least partially inside the body.

In the case of the description used "on" the body, there are understood here all the corresponding objects which are known to the person skilled in the art and which can be worn on the body, e.g. watches, parts for watches, such as e.g. case, bezel, bracelet, locking mechanisms for watches and the like, but also all types of jewellery, such as e.g. rings, bangles, bracelets, chains and the like.

In the case of the description used "partially inside" the body, there are understood here all corresponding objects which are known to the person skilled in the art and which can be worn partially inside the body, such as e.g. earrings, earstuds and all types of piercings and the like.

In the case of the description used "inside" the body, there are understood here all corresponding objects which are known to the person skilled in the art and which can be introduced inside the body, e.g. implants, in particular medical implants, such as e.g. artificial joints, or stabilising plates screwed onto bones, nails integrated in bones and the like. Since also with all types of implants, there exists direct, and above all, permanent body contact with the relevant object, hence a nickel-free, corrosion-resistant and rigid material is of the greatest advantage in order to avoid allergic reactions or sensitivity problems and in order to produce in particular long-life implants.

Generically, also the terms "indirect body contact" and "direct body contact" can also be used.

According to the invention, the biocompatible material hence consists of a rust-resistant, alloyed chromium steel which is configured to be nickel-free and has at least one martensitic surface layer, this martensitic surface layer being achieved by a change in the structural state from ferrite via austenite to martensite. This martensitic surface layer is furthermore distinguished by the fact that, orthogonally to the surface into the sample interior, it displays a virtually linear course of the accompanying hardness.

It is essential to the invention in the case of the biocompatible material according to the invention in addition that the material is finished completely mechanically before the heat treatment, i.e. is in a ready-for-sale state. The reason resides in the fact that, on the one hand, mechanical machining taking place after the heat treatment (intended here are all non-cutting machinings, such as e.g. punching and bending, and all machinings with the formation of chips, such as e.g. milling, turning, grinding, boring) would become virtually impossible because of the adjusted hardness, and, on the other hand, subsequent mechanical machining could remove and/or pierce the produced surface layer relatively rapidly, and hence the protection of the biocompatible material according to the invention relative to corrosion and scratching would be lost.

This means that, for example in the case of preferred polished and/or matt and/or roughened end products of a biocompatible material, such as e.g. watches/parts for watches, jewellery and implants, must be correspondingly finished, i.e. polished or made matt or roughened, before the heat treatment. After the heat treatment, the surface of the material—if desired—can subsequently be polished lightly once again and/or made matt and/or roughened as a result of a "slight tarnishing" (matting caused by the process) in order to obtain again the desired surface before the heat treatment. Despite this additional heat treatment and subsequent retreatment, possibly undertaken, the production costs are virtually the same as with the austenitic steels used at present for objects with indirect or direct body contact, such as watches/parts for watches, jewellery and implants, since the ferritic and/or ferritic/martensitic and/or martensitic chromium steels are significantly cheaper because of the lack of the nickel component.

Objects made of such a biocompatible material can advantageously be disposed on and/or partially inside the body and/or completely inside the body or indirectly or directly on the human body as a result of the freedom from nickel.

In the case of the biocompatible material, it is thereby preferred if the hardness difference between the surface hardness of the surface layer to the lowest hardness of the core is 130 to 350%. The surface hardness of the martensitic surface layer after the heat treatment is in the range of 500 to 750 HV3 and the smallest hardness of the core in the case of a ferritic stainless steel is in the range of 160 to 260 HV3 and the lowest hardness of the core in the case of a martensitic stainless steel is in the range of 400 to 560 HV3. The detectable increase in hardness in the range of up to 750 HV offers scratch-resistance, which is improved by at least 150 times, according to the scratch and wear-resistance test SOP 3-SRC of the research institute in Schwäbisch Gmünd.

By using the chromium steels according to the invention, an approximately identical corrosion-resistance as with austenitic 1.4301 or 1.4404 steels is achieved, with approximately the same production costs and a scratch-resistance which is improved by at least 15.000% and the simultaneous important freedom from nickel. In addition, the machinability relative to austenitic steels is significantly better since a shorter chip and hence automated machinability is possible with the chromium steels according to the invention. Hence the production costs can be reduced in addition, besides the use of the significantly cheaper chromium steel according to the invention relative to the significantly more expensive austenitic steel.

Should the ferritic or martensitic samples have a thickness of approx. less than 0.7 mm, then in this case also complete full-hardening can be achieved so that the hardness penetration depth of the surface layer is completely penetrable and hence these samples, starting from the surface up to the core and hence over the entire sample cross-section, display a virtually linear hardness course, i.e. in this case a penetrable martensitic region, since the heat treatment is effected on both sides or all sides.

Also in the case of ferritic samples with a thickness between greater than approx. 0.7 mm to approx. 3 mm, it is conceivable, since the heat treatment is effected on both sides or all sides, that a pure ferritic core region with corresponding initial hardness of the untreated material is no longer present but, in this case, the sample, by incorporating nitrogen and the subsequent quenching, finishes up in an intermediate hardness (mixed hardness) between martensite hardness and core hardness, i.e. at a higher hardness. The penetration depth of the outer martensitic region (surface layer) remains approximately the same but the ferritic-martensitic region (transition region) is shortened because of the higher mixed hardness and the linear decrease in the transition region. This applies analogously for martensitic samples with the difference that the transition region here is configured to be martensitic with decreasing nitrogen concentration and the hardness finishes up correspondingly in an intermediate hardness greater than the initial hardness.

In the case of the biocompatible material, it is preferred if the surface of the martensitic surface layer is roughened and/or made matt and/or polished and/or untreated. The surface roughness can thereby be in the range of 0.01 μm to 4.0 μm.

If the surface of the biocompatible material is untreated after the heat treatment, i.e. it is not polished, made matt or roughened, the scratch-resistance is increased even further since higher hardness peaks on the surface arise after the heat treatment and are not removed. By omitting a subsequent surface treatment, the variable costs could be reduced even further and a new surface design could be achieved (description: e.g. "satinised" or "new satin").

From a material point of view, there can be used in the biocompatible material according to the invention, in principle all rust-resistant, alloyed stainless steels which are nickel-free and not austenitic. Examples of these are all the steel groups with the material numbers 1.40xx, 1.41xx, 1.45xx, 1.46xx, and 1.47xx which have no nickel alloyed in them.

The letters x here indicate respectively a number between 0 and including 9-according to the steel code, expanded edition 2007.

Examples: 1.4000, 1.4001, 1.4002, 1.4005, 1.4007, 1.4009, 1.4010, 1.4015, 1.4016, 1.4021, 1.4024, 1.4028, 1.4029, 1.4031, 1.4034, 1.4035, 1.4036, 1.4037, 1.4085, 1.4086, 1.4104, 1.4105, 1.4106, 1.4109, 1.4110, 1.4111, 1.4112, 1.4113, 1.4116, 1.4117, 1.4119, 1.4125, 1.4126, 1.4133, 1.4136, 1.4138, 1.4153, 1.4509, 1.4510, 1.4511, 1.4513, 1.4520, 1.4521, 1.4523, 1.4525, 1.4526, 1.4528, 1.4535, 1.4590, 1.4592, 1.4595, 1.4601, 1.4602, 1.4603, 1.4604, 1.4605, 1.4724, 1.4725, 1.4735, 1.4736, 1.4742, 1.4746, 1.4748, 1.4749, 1.4760, 1.4761, 1.4762, 1.4763, 1.4765, 1.4767, 1.4768 and 1.4783.

Of course all future stainless steels which are at present not yet included in the steel code are intended to be herewith included. The steels 1.4016 or 1.4021 are preferred.

By means of a martensitic surface layer, a significant increase in hardness results, with which superior properties with respect to scratch- and corrosion-resistance which, in addition to the extremely important freedom from nickel, are achieved with approximately the same production costs.

The formation of the martensitic surface layer can be effected in the case of the biocompatible material by a heat treatment, preferably by a so-called "nitrogen case hardening". The chromium steel must preferably have a chromium proportion of at least 12%. The nitrogen case hardening of steel materials is known per se in prior art and is described for example in EP 0 652 300 A1 or also in DE 40 33 706.

In the case of surface nitrogen case hardening, the procedure thereby is such that the steel material is treated at a temperature between 1000° C. and 1200° C. in a nitrogen-containing gas atmosphere for between 3-6 hours and subsequent cooling.

Surprisingly, it was now shown that such a method, when applied on a completely mechanically finished biocompatible material, i.e. on a nickel-free chromium steel, leads to superior properties.

The invention is described subsequently in more detail with reference to the FIGS. 1a, 1b, 1c, 1d and 1e without restricting the subject of the invention hereto. The diagrams are represented in an idealised form and can of course deviate from the represented form in their course.

BRIEF DESCRIPTION OF DRAWINGS

FIG. 1a shows a hardness course with a component thickness of 5.00 mm

FIG. 1b shows a hardness course with a component thickness of 1.5 mm.

FIG. 1c shows a penetrable hardness course with a component thickness of 0.5 mm.

FIG. 1d shows a transverse section through heat-treated ferrite steel.

DETAILED DESCRIPTION

Figure 1E:
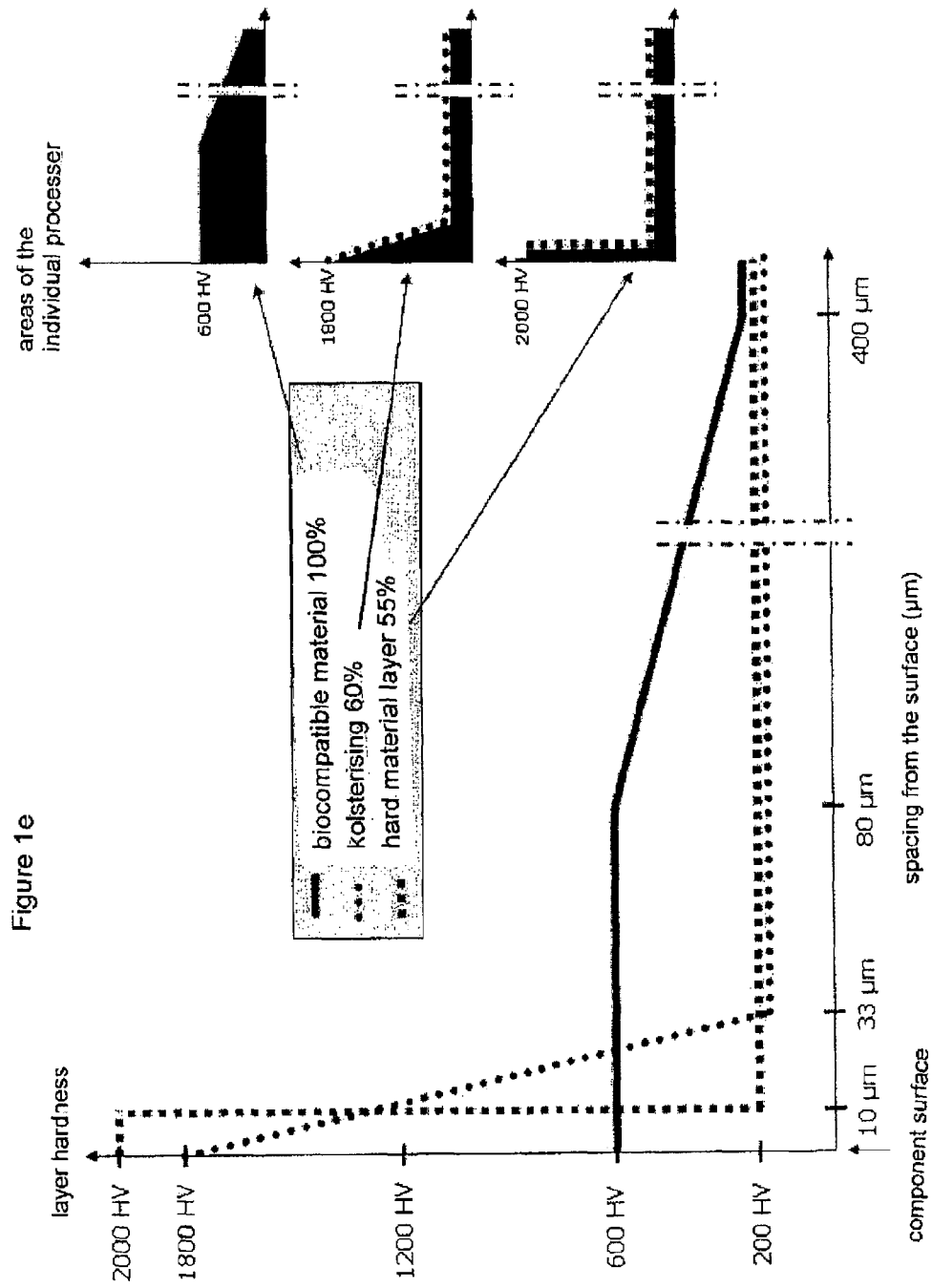
FIG. 1e shows a direct comparison of described methods and new method.

FIG. 1a shows the hardness course after a heat treatment with the example of a ferritic chromium steel and a martensitic chromium steel in the form of a graphic illustration.

In the case of martensitic chromium steels, the surface layer is equivalent to that in the case of ferritic chromium steels, i.e. it consists of a martensitic structure. The transition zone, in contrast, differs since it shows no ferritic-martensitic structure in this case but is distinguished by a martensitic structure with a nitrogen concentration which decreases towards the sample interior.

In the example case according to FIG. 1a, a ferritic (1.4016) and a martensitic sample (1.4021) with a thickness of 5 mm is nitrogen case hardened with nitrogen at temperatures of above 1050° C. and quenched or deep-cooled and annealed.

The material 1.4016, X6 Cr 17 is a ferritic chromium steel with less than or equal to 0.08% carbon. By incorporating nitrogen, the result is conversion into austenite, martensite being produced during the subsequent quenching, which can be seen as in FIG. 1d, reducing towards the core corresponding to the inclusions. Obviously, a virtually complete phase conversion, i.e. a so-called austenitising, is achieved due to the high temperature treatment with variable process pressures and nitrogen absorption. The cubically space-centred deep-temperature phase α (ferrite) is thereby converted completely into the cubically surface-centred high temperature phase γ (austenite). The subsequent quenching/supercooling is effected so rapidly that diffusion processes do not occur and that the structure flips over into martensite. This greatly tempered lattice leads to the already portrayed increase in hardness of the material. As a result, this leads to a complete structural change occurring at least in the region near to the surface. This also emerges from the examples, in particular from FIG. 1a. As this example shows graphically, the hardness course of the steel material according to the invention is configured with sufficiently thick samples greater than 3 mm such that, starting from the surface in the direction of the inner ferrite core, there results hereby in the martensitic surface region a virtually linear transition zone and, in the ferritic-martensitic transition zone, a continuous change in the structural state and hence also the accompanying change in hardness.

As emerges from FIG. 1a, the ferritic sample made of 1.4016 has a surface hardness of approx. 650 HV 3. The hardness penetration depth in the example case is 150 μm. Calculation of the hardness penetration depth is implemented according to the invention such that it starts from the lowest hardness of the core likewise measured in HV3+30%. Hence, the initial value in the example case is 200 HV 3. The surface layer of such a sample with a thickness of greater than approx. 3 mm, 5 mm in the example case, shows, starting from the surface in the direction of the sample centre, within the surface layer (martensitic region=1)) a virtually linear hardness course and, in the abutting transition zone (martensitic-ferritic region=2)), a continuous decrease in accompanying hardening up to the core hardness (ferritic region=3)), 200 HV 3 in the example case. FIG. 1a shows furthermore the hardness course of a martensitic chromium steel. This material 1.4021, X20 Cr 13 is a martensitic chromium steel with 0.16 to 0.25% carbon. In comparison with the ferritic chromium steel, this steel, after accompanying heat treatment, has, because of the higher carbon component, a somewhat greater linear hardness with up to 750 HV (approx. 700 HV 3) in the example case inside the surface layer=1) and an analogous continuous decrease in hardness inside the transition zone=2) up to the core hardness thereof (after the heat treatment) of approx. 500 HV 3.

In both cases, a great advantage becomes clear relative to the methods described in prior art which display an abrupt change in the hardness course and the structural state, i.e. a phase boundary.

It emerges from FIG. 1b that, in the case of a ferritic sample made of 1.4016 with a thickness between 0.7 mm and less than approx 3 mm, 1.5 mm in the example case, it is possible because of the heat treatment on both sides or all sides that there is no longer a ferritic core region but instead the hardness in the sample interior, due to the incorporation of nitrogen and the subsequent quenching, finishes up in an intermediate hardness (=mixed hardness) between martensite hardness and initial hardness. This means that the core hardness in this case does not decrease to the initial hardness of the untreated ferritic material but finishes up correspondingly at a higher hardness (400 HV 3 in the example case) and subsequently increases again in cross-section continuously to the martensite hardness of the surface layer=1), 650 HV 3 in the example case. The martensitic region=surface region=1) remains, in the example case, equal to a penetration depth of approx. 150 μm, however the transition region=2) shortens because of the higher intermediate hardness (=mixed hardness) of the sample interior and of the linear decrease of the transition region from approx. 450 μm to approx. 300 μm. The same applies for martensitic samples, only that in the example case here the intermediate hardness (=mixed hardness) in the sample interior is set at approx. 550 HV and subsequently increases analogously in cross-section again continuously to the martensite hardness of the surface layer=1), 700 HV 3 in the example case. The martensitic region=edge region=1) remains, in the example case, equal to a penetration depth of approx. 150 μm, the transition region=2) shortens analogously because of the higher intermediate hardness (=mixed hardness) of the sample interior and of the linear decrease in the transition region.

As emerges from FIG. 1c, it is of course possible in the case of sufficiently thin ferritic samples made of 1.4016 with a thickness of approx. less than 0.7 mm, 0.5 mm in the example case, that complete hardening is achieved, i.e. the hardness penetration depth of the surface layer is completely penetrable and martensitic=1) so that these samples, starting from the surface towards the core and hence over the entire sample cross-section, display a continuous virtually linear, i.e. a constant hardness course, 650 HV 3 in the example case. The same applies to martensitic samples of this order of magnitude, i.e. complete hardening is also achieved here with a constant hardness course, 700 HV 3 in the example case.

It can be said basically, with respect to FIG. 1a, that naturally also other phases, such as e.g. perlite and bainite in the core structure=3), can be possible as a function of the component size and the cooling rate.

FIG. 1d shows very clearly, in a transverse section of a heat-treated ferritic sample made of 1.4016, in the enlargement 50:1, the structural configuration from which the martensitic surface layer can be detected. Likewise, the transition zone made of a mixture of ferrite and martensite grains can be detected very well. The treated surface thereby has an average grain diameter of 28 to 40 μm, measured according to the linear intercept method. The grain diameter of the treated part in the core is 15 to 20 μm and that of the untreated initial material 10 to 14 μm.

The transverse section illustration of a heat-treated martensitic sample was not undertaken since, because of the penetrable martensitic structure, neither the surface layer and transition zone nor the core could be differentiated.

FIG. 1e shows, on the one hand, the direct comparison of the presently known—and already adequately described methods (hard material layers, Kolsterising) and the new method illustrated here with respect to a biocompatible material and the average layer thicknesses which can be achieved therewith and have corresponding hardness courses. And on the other hand, the respective integrated areas of the described methods which reflect a measure for the resistance against point loading (impact-strength) are illustrated. The area which is achieved with the biocompatible material was hereby fixed at 100% and the other methods were calculated in contrast corresponding to their areas. As can be detected therefrom clearly, the biocompatible material described here can withstand a mechanical point loading which tends to be greater by 40% than the other two methods which display a virtually abrupt decrease, i.e. a phase boundary of the accompanying hardening.

Surprisingly, it was now established that the biocompatible material with the above-described surface configuration, has corrosion-resistances and scratch-resistances which are superior due to a phase conversion/austenitising close to the surface, with simultaneous desired absolute freedom from nickel and approximately the same production costs.

As a result, it can hence be established that the biocompatible material consists of a rust-resistant, alloyed chromium steel which is configured to be absolutely nickel-free and in the case of which, as a function of the sample thickness, at least the surface layer is however configured to be martensitic, the martensitic surface layer, orthogonally to the surface into the sample interior, displaying a virtually linear course of the accompanying hardening and is achieved by a change in the structural state from ferrite via austenite to martensite and the corresponding material is in contact preferably on and/or partially inside the body and/or completely inside the body or indirectly or directly with the human body. Furthermore, the biocompatible material according to the invention is distinguished by virtually the same production costs. The biocompatible material according to the invention, which is in contact preferably on and/or partially inside the body and/or completely inside the body or indirectly or directly with the human body, is therefore distinguished predominantly by the fact that, in combination, it has at the same time the same production costs, freedom from nickel, high scratch-resistance and corrosion-resistance.

The invention claimed is:

1. A watch, comprising:
   a biocompatible material including:
   a rust-resistant, alloyed stainless steel; and
   at least one martensitic surface layer formed by a heat treatment with nitrogen case hardening and subsequent cooling,
   wherein orthogonally to a surface into a sample interior, the martensitic surface layer displays a virtually linear course of the accompanying hardening and the stainless steel is nickel-free.

2. The watch of claim 1, wherein the martensitic surface layer is achieved by a complete phase change in a structural state from ferrite via austenite to martensite.

3. The watch of claim 1, wherein the material is completely mechanically finished before the heat treatment.

4. The watch of claim 1, wherein the martensitic surface layer has a thickness of at least 20 μm.

5. The watch of claim 1, wherein the steel is selected from steel groups with material numbers 1.40xx, 1.41xx, 1.45xx, 1.46xx and 1.47xx.

6. The watch of claim 1, comprising:
   an additional transition zone displaying a continuous decrease in the accompanying hardening.

7. The watch of claim 1, wherein the surface hardness of the surface layer is in a range between 500 and 750 HV 3.

8. The watch of claim 1, wherein the watch is in direct contact with the human body.

9. The watch of claim 1, wherein the watch is in indirect contact with the human body.

10. The watch of claim 1, wherein the watch includes at least one of a case, a bezel, a bracelet and a locking mechanism.

11. A jewelry, comprising:
    a biocompatible material including:
    a rust-resistant, alloyed stainless steel; and
    at least one martensitic surface layer formed by a heat treatment with nitrogen case hardening and subsequent cooling,
    wherein orthogonally to a surface into a sample interior, the martensitic surface layer displays a virtually linear course of the accompanying hardening and the stainless steel is nickel-free.

12. The jewelry of claim 11, wherein the jewelry is one of a ring, a bangle, a bracelet, a chain, earrings, earstuds and body piercings.

13. An implant, comprising:
    a biocompatible material including:
    a rust-resistant, alloyed stainless steel; and
    at least one martensitic surface layer formed by a heat treatment with nitrogen case hardening and subsequent cooling,
    wherein orthogonally to a surface into a sample interior, the martensitic surface layer displays a virtually linear course of the accompanying hardening and the stainless steel is nickel-free.

14. The implant of claim 13, wherein the implant is one of an artificial joint, a stabilizing plate screwed onto bones, and a nail integrated in bones.

* * * * *